United States Patent
Enarson

(10) Patent No.: US 6,459,251 B1
(45) Date of Patent: Oct. 1, 2002

(54) METHOD AND DEVICE FOR MEASURING CONCENTRATION

(76) Inventor: Knut Enarson, Ängsgatan 18, S-661 42 Säffle (SE)

(*) Notice: Subject to any disclaimer, the term of this patent is extended or adjusted under 35 U.S.C. 154(b) by 0 days.

(21) Appl. No.: 09/581,484

(22) PCT Filed: Dec. 7, 1998

(86) PCT No.: PCT/SE98/02234

§ 371 (c)(1),
(2), (4) Date: Jun. 13, 2000 Jun. 13, 2000

(87) PCT Pub. No.: WO99/36761

PCT Pub. Date: Jul. 22, 1999

(30) Foreign Application Priority Data

Dec. 29, 1997 (SE) ................................. 9704899

(51) Int. Cl.⁷ ............................................. G01N 27/00

(52) U.S. Cl. .................. 324/71.4; 73/53.03; 73/61.71; 73/61.73

(58) Field of Search ........................ 324/71.4; 209/207, 209/208, 209, 210; 210/513, 519, 521; 73/53.04, 53.07, 54.21, 54.31, 54.32, 61.59, 61.73, 53.03, 61.41, 61.71

(56) References Cited

U.S. PATENT DOCUMENTS

| | | | | |
|---|---|---|---|---|
| 3,812,984 A | * | 5/1974 | Cladingboel | 214/15 B |
| 3,837,216 A | * | 9/1974 | Shinohara | 73/61 R |
| 3,965,608 A | * | 6/1976 | Schuman | 43/110 |
| 4,156,584 A | * | 5/1979 | Schuck | 417/435 |
| 4,284,496 A | * | 8/1981 | Newton | 209/3.3 |
| 4,467,637 A | * | 8/1984 | Rumberger | 73/61 R |
| 4,527,947 A | * | 7/1985 | Elliot | 415/121 B |
| 4,818,414 A | * | 4/1989 | Ross | 210/744 |
| 4,840,729 A | * | 6/1989 | Levine | 210/170 |
| 5,199,848 A | * | 4/1993 | Kapich | 415/202 |
| 5,346,629 A | * | 9/1994 | Wuller | 210/739 |
| 5,546,791 A | * | 8/1996 | Meeten | 73/54.28 |
| 5,561,520 A | * | 10/1996 | Williams | 356/335 |
| 5,569,844 A | * | 10/1996 | Sowerby | 73/61.75 |
| 5,834,635 A | * | 11/1998 | Preikschat et al. | 73/53.01 |
| RE36,074 E | * | 2/1999 | Kouzuki | 324/71.4 |
| 6,207,015 B1 | * | 3/2001 | Templer et al. | 162/189 |

FOREIGN PATENT DOCUMENTS

| | | |
|---|---|---|
| EP | 0 383 622 | 8/1990 |
| SE | 300 356 | 4/1968 |
| WO | WO 91/04480 | 4/1991 |
| WO | WO 96/16322 | 5/1996 |

* cited by examiner

*Primary Examiner*—N. Le
*Assistant Examiner*—Etienne P LeRoux
(74) *Attorney, Agent, or Firm*—Akerman Senterfitt

(57) ABSTRACT

A device for measuring concentration of a flowing suspension wherein a moveable detector body (3) is arranged for detecting the resistance against movement in the suspension, and including a flow modifying element (4) for bringing a portion of the suspension which is representative of the concentration of the suspension flow to the region of the detector element (3). The invention is distinguished by the flow modifying element being a fixed deflector (4), which is arranged to deflect a boundary layer (7) of the suspension flow closest to the conduit wall (1) such that it is brought away from the region of the detector body (3). The invention also concerns a method for measuring concentration and a deflector.

19 Claims, 2 Drawing Sheets

METHOD AND DEVICE FOR MEASURING CONCENTRATION

Figure 1:
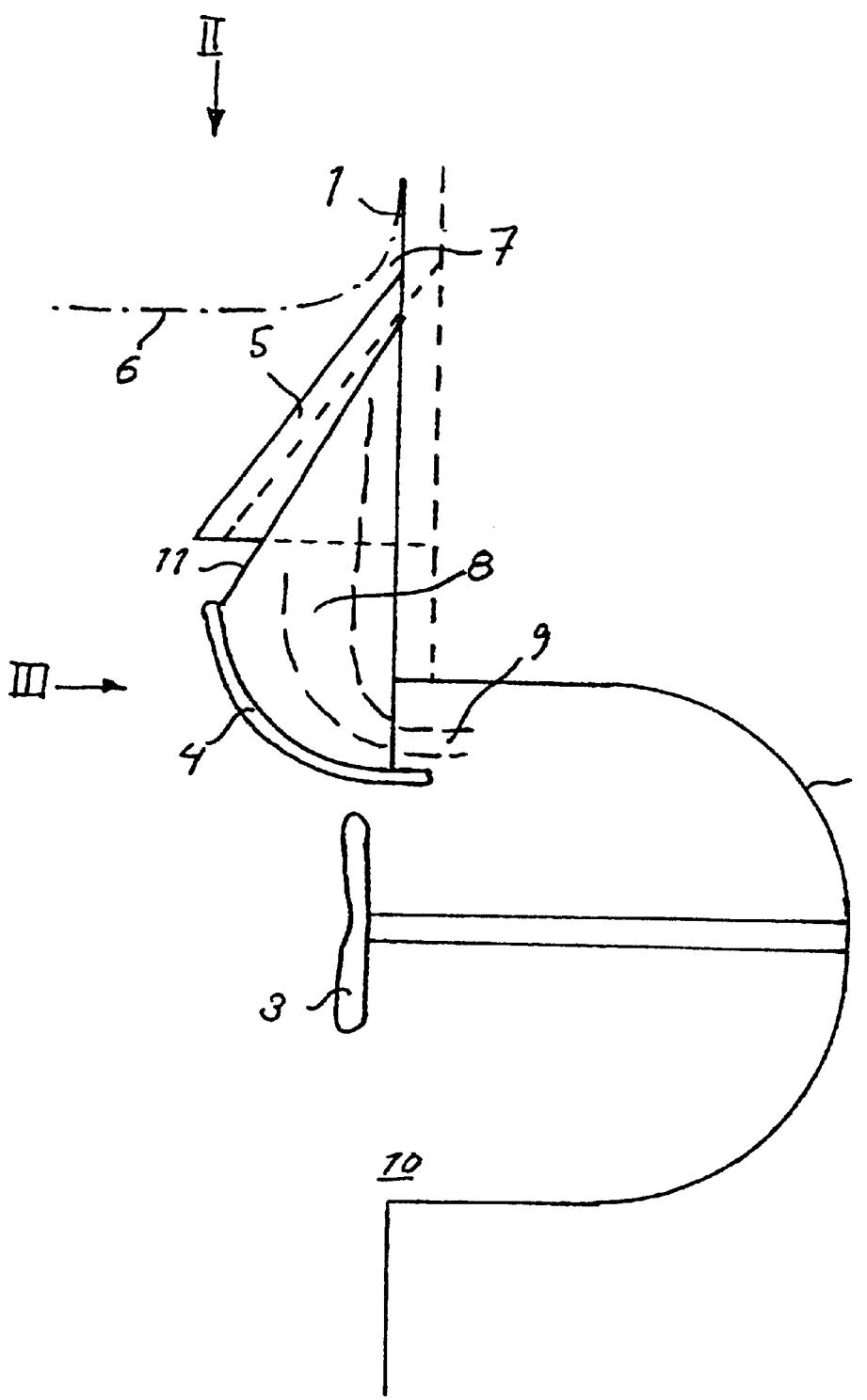

This invention concerns a method and an apparatus for measuring concentration.

A suspension is a fluidum including at least two components i.e. a liquid and solid particles. With respect to pulp suspensions for paper manufacture, the liquid is substantially water and the solid particles are fibres and possibly fillers, chemicals and impurities.

When a suspension flows through a conduit as created a boundary layer adjacent to the conduit wall, where the flow velocity is low, closest to the conduit wall the velocity is practically zero. For reasons of flow physics, a two-component fluidum such as a suspension will contain more liquid in the boundary layer, meaning that the concentration of solid particles is lower in the boundary layer than in the main flow of the suspension.

For this reason suspension concentration measurements with respect to solid particles has to be made in the main flow or a flow which is representative of the concentration of the main flow. The latter is commonly applicable in respect of pulp suspension measurements after a shut down, when the conduit has been emptied from water and pulp, whereby a dried pulp fibre plug is usually formed, which when restarting the plant affects unprotected instruments inside the conduit, or in respect of unscreened suspension where unsolved pieces brought along with the suspension might damage the gauge and/or permanently affect the result of the measurement.

To this end it is previously known to place the gauge inside a side mounted bulb, where the detector element is placed protected from said possible harmful impurities. However, since the bulb is attached to the conduit wall it will to a great expend be fed with the boundary layer if no particular measures are taken, and therefore a concentration level which is not representative of the main flow will prevail inside the bulb. This condition results in measurement errors resulting in important economic drawbacks. For this reason, devices of this kind has been provided with a propeller which feeds the concentration of the main flow into the bulb and thus to the region of the detector element.

The prior art, for this reason, demands the use of an important pumping effect in order to somehow ensure that the main flow concentration will be brought into the bulb, in particular if great flows are normally present in the conduit, which is the case with respect to pulp suspensions. This results in considerable energy consumption, need for a powerful motor installation and servicing and maintenance for this installation including several devices and moveable parts. Using the prior art is also a risk of the supply from the main flow being insufficient or uneven. Erroneous measurement results can therefore not be excluded.

It is an aim of this invention to avoid the drawbacks of the prior art and to provide a method and a device allowing a reliable and economic solution.

By the boundary layer of the suspension flow, which is closest to the conduit wall, being deflected, it is brought away from the region of the detector element, which in turn is located in the outer area of, or outside the main extension path of the conduit, and this is achieved by a flow modifying element being a fixed deflector, it is ensured that the boundary layer influence on the pulp concentration measurements are eliminated. Contrary to the prior art the deflection is not obtained by an outside power source but instead by the propulsive power imparted to the main flow by the normal propulsive pump.

Since the boundary layer has been deflected in the region of the detector element it will operate in the suspension concentration prevailing in the main flow which gives essentially safer measurement results. It could be mentioned that it is desirable, in the prior art as well as with respect to the invention, to carry out the detection in the suspension conduit such that the flow is disturbed as little as possible in order to avoid unnecessary losses in the flow. I.e. located at the side of the conduit. A careless placement of the detector extending too far into the conduit could also result in plugging of the conduit, resulting from collecting of possibly flowing unsolved objects, beside damages on the detector, as is discussed above.

The feature of a protective bulb, results in enhanced safety for the detector element against damages and unwanted influences and allows reduced effect on the stream in the conduit. By the boundary layer being directed into the bulb, a detector element being arranged in the region of the mouth of the bulb can safely operate in a pulp concentration which is representative of the main flow.

By the deflector being curved in the direction the inside of the bulb, the flow conditions are enhanced, which is accentuated if the intake area of the deflector exceeds the outflow area. The latter results in increased velocity at the entrance of the boundary layer into the bulb, so that its flow inside the bulb is promoted. For this purposes the bulb has suitably been given an even curve so that the boundary layer safely flows along the outside wall of the bulb from the deflector to the "downstream side" of the bulb. In particular, concerning pulp suspensions, there is normally a relatively high pressure present in the conduit and for this reason the bulb must be constructed to withstand this pressure, which results in that it is usually designed with double-curved surfaces as often as possible.

By arranging a screen upstream from the deflector, it is ensured that possible larger impurities following the stream are brought away from the inlet of the deflector, so as to prevent plugging. The screen is suitably arranged such that the distance between the screen elements are smaller than the distance between the deflector plate and the wall of the conduit and the bulb, thus minimising the risk of plugging. It is preferred that the screen is comprised of repulsive means extending from the conduit wall a distance upstream from the deflector and extending towards the inside of the conduit, e.g. linearly. At the position of the detector they provide the same extension into the conduit as the deflector or an inward extension exceeding that of the deflector. A simple screen may be comprised of a number of triangular plates being distributed along the width of the deflector and having a pointed corner applied against the conduit wall being directed against the flow direction.

Figure 2:
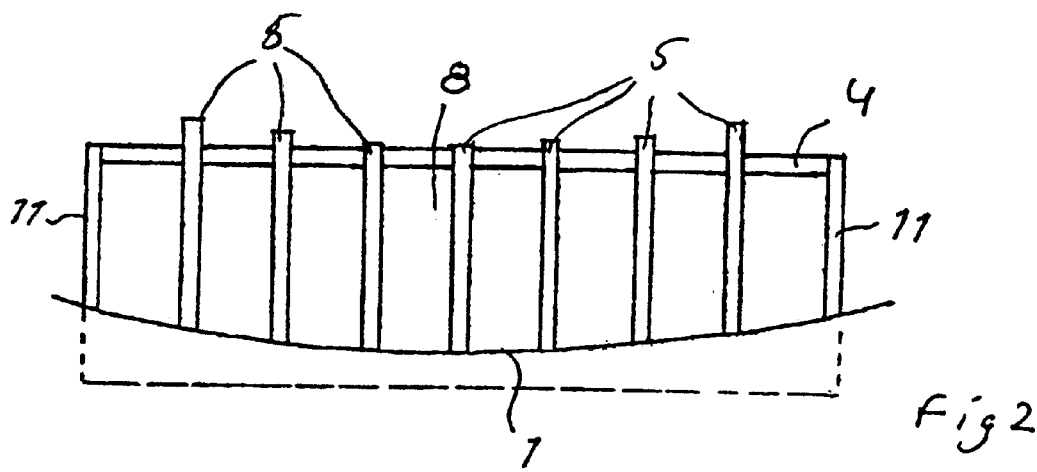
Figure 3:
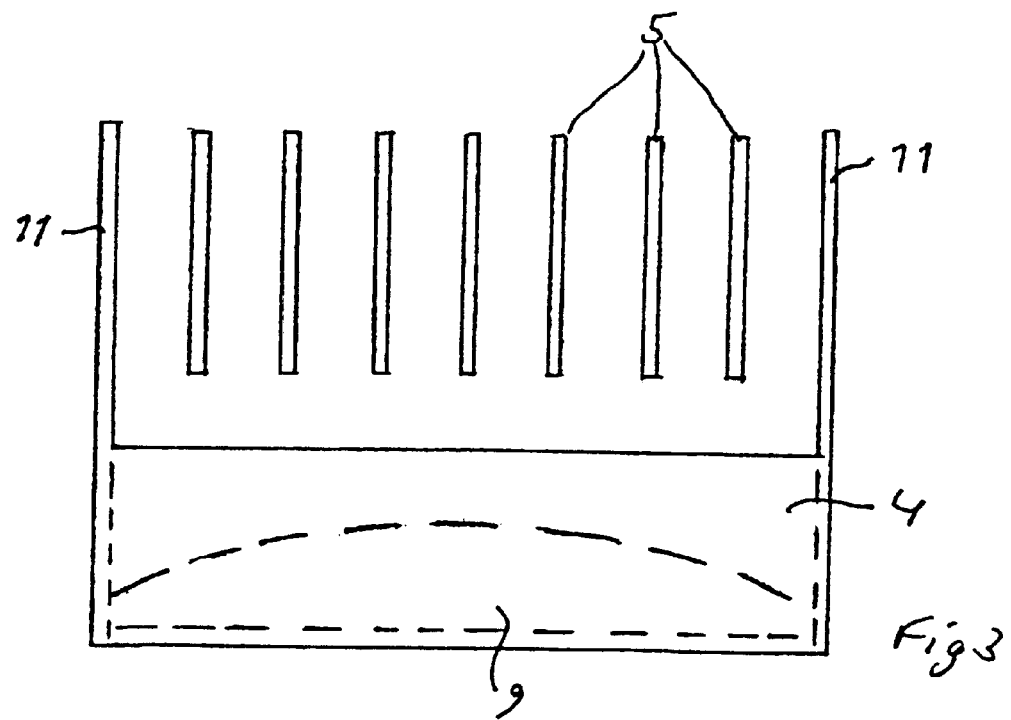

The invention will now be described in greater detail at the background of a preferred embodiment and with reference to the annexed drawing wherein:

FIG. 1 shows a device in respect of a conduit including a deflector according to the invention in an axial section, FIG. 2 shows the device of FIG. 1 in a cross section through the conduit as seen in the direction of arrow II in the same Figure, and FIG. 3 shows the device of FIG. 1 as seen in the direction of the arrow III in the same Figure.

In FIG. 1, 1 indicates a conduit for transporting a pulp suspension including water and solids such as pulp fibres, fillers etc. The conduit 1 is provided with a bulb 2 mounted at its side which in the region adjoining the conduit provides a detector element 3 for rotation in the suspension. The detection is carried out in a per se known manner such that the rotational resistance of the detector element in the suspension is detected and used as a measurement on the concentration of the suspension.

Upstream the detector element there is arranged a deflector 4, which is comprised of a metal plate profile, in this case having a cross section essentially corresponding to a quarter of a circular arc. The dimension of the deflector as seen crosswise from the wall of the conduit 1 is adapted such that a boundary layer 7 of the suspension flowing through the conduit is deflected by the deflector 4 such that after the deflection it will attain a horizontal movement at the outlet of the deflector as shown in the Figure with interrupted lines and indicated with 9, so that said boundary layer is brought to the inner part of the bulb 2 for flow along the inner wall of the bulb and for finally leaving the bulb at 10 and be brought back to the main flow in the conduit 1. By arranging the deflector 4 such that the inlet area at 8 exceeds the outlet area at 9, an increased speed of the boundary layer is obtained resulting in favourable flow along the bulb wall 2.

Upstream the deflector 4, a number of screen elements 5 are distributed along the width of the deflector, which elements in this case are comprised of triangular plates having an increasing cross section as seen in the flow direction, so that possible larger impurities such as unsolved twigs etc are pushed away from the deflector, thus avoiding plugging. 6 indicates the flow velocity distribution of the suspension as seen across the width of the conduit, showing that the velocity provides small variation of the main part of the cross section of the conduit except at the boundary layer 7, where the speed close to the conduit wall is lower and closest to the wall is zero. Because of the construction of the deflector, downstream the deflector there will be brought in a suspension portion being in the main stream, which results in that the detector element 3 operates in a portion of the suspension having a concentration which is representative of the concentration of the suspension as a hole. 11 indicates the fastening devices for the deflector 4, in this case consisting of two plates, which are suitably connected to deflector 4 along its extension, and further comprises upwardly extending portions which are intended for fastening on the inside of the wall of the conduit 1, for example by welding.

The deflector 4 in the embodiment is a part of a cylinder, which is more evident from FIG. 2, which simplifies the manufacture. In this Figure there are also shown the fastening elements 11 and the screen elements 5 which are distributed over the inlet surface 8 of the deflector.

From FIG. 3 again, the distribution of the screen elements are shown wherein a certain distance is provided between these elements and the inlet end of the deflector. From this Figure the fastening elements 11 are shown as well as the outlet surface 9 of the deflector 4.

The invention is not limited to the above embodiment but may be modified with respect to shape and method of fastening. In certain cases a solution is thus applicable wherein the deflector is not co-operating with a bulb, but instead provides a plough-like construction having plates extending against the inside of the conduit and inwardly and upwardly, and behind which, a detector element is arranged to operate. Such a plough-like deflector deflects the boundary layer sideways from the detector element such that a representative portion of the suspension is allowed to flow from the main stream into the region of the detector element.

When measuring concentration in connection with the device according to the invention, in many applications the detector element will be operating in a flow having a cross wise component with respect to the axis of the detector element. In order to enhance the measurement accuracy, the detection method may be controlled such that measurement is made when the detector body, usually being analogous to a twin blade propeller, is essentially in line with the flow direction and thus the measurement is not effected against said cross wise component.

The deflector may also be constructed otherwise, for example having a double-curved surface, whereby closer connection to the conduit wall and the bulb wall respectively, may be obtained. It is further not excluded to construct the deflector as a plane plate or at least having a linear cross section, whereby for example it is placed essentially at the location of the deflector 4 in FIG. 1, but having a linearly extending cross section. Also the screen elements may be shaped differently, for example as a rods of the like. When measuring a suspension, which is free from impurities such as screened pulp, the screen elements may also be excluded.

What is claimed is:

1. A method for measuring a concentration of a suspension of solid particles in a liquid flowing through a conduit, comprising the steps of:

providing a detector element in the conduit which is moveable in the suspension inside the conduit;

detecting the resistance against movement of the detector element;

protecting the detector body from objects existing in and flowing along with the suspension; and deflecting a boundary layer of the suspension flow which is closest to the conduit wall away from the region of the detector body.

2. A device for measuring a concentration of a suspension of solid particles in a liquid that is flowing in a conduit, comprising:

a detector element that is moveable in the suspension and arranged at a side of the conduit for detecting resistance against movement of the detector element in the suspension flowing in the conduit;

means for protecting the detector element from objects existing and flowing along with the suspension; and a fixed deflector for deflecting a boundary layer of the suspension flow that exists closest to the conduit wall away from the region of the detector element.

3. The device according to claim 2, further comprising a protective bulb, which is mounted on a side of the conduit in the region of the detector element.

4. The device according to claim 3, wherein the deflector is placed at the upstream side of the bulb in order to direct the deflected boundary layer of the suspension flow into the bulb.

5. The device according to claim 4, wherein the deflector is curved as seen in an axial section through the conduit and through the bulb such that a first portion of the deflector is directed against the flow direction of the conduit and a second portion into the bulb.

6. The device according to claim 5, wherein the area between the first portion and the conduit wall adjacent thereto is greater than the area between the second portion and the bulb wall adjacent thereto in order to obtain increase in velocity of the flowing boundary layer.

7. The device according to claim 2, wherein the means for protecting the detector element is a screen element for preventing larger impurities from entering the deflector.

8. The device according to claim 6, wherein said screen elements comprise elements having increasing cross section inwardly into the conduit as seen in the flow direction.

9. A deflector for application into a device according to claim 2.

10. The device according to claim 3, wherein the means for protecting the detector element is a screen element for preventing larger impurities from entering the deflector.

11. The device according to claim 4, wherein the means for protecting the detector element is a screen element for preventing larger impurities from entering the deflector.

12. The device according to claim 5, wherein the means for protecting the detector element is a screen element for preventing larger impurities from entering the deflector.

13. The device according to claim 5, wherein the means for protecting the detector element is a screen element for preventing larger impurities from entering the deflector.

14. A deflector for application into a device according to claim 3.

15. A deflector for application into a device according to claim 4.

16. A deflector for application into a device according to claim 5.

17. A deflector for application into a device according to claim 6.

18. A deflector for application into a device according to claim 7.

19. A deflector for application into a device according to claim 8.

* * * * *